(12) United States Patent
Iwamoto et al.

(10) Patent No.: US 8,262,877 B2
(45) Date of Patent: Sep. 11, 2012

(54) GLASS ELECTRODE AND SENSITIVE GLASS FOR THE GLASS ELECTRODE

(75) Inventors: Yasukazu Iwamoto, Kyoto (JP); Yuji Nishio, Kyoto (JP)

(73) Assignee: HORIBA STEC, Co., Ltd., Kyoto-shi (JP)

( * ) Notice: Subject to any disclaimer, the term of this patent is extended or adjusted under 35 U.S.C. 154(b) by 355 days.

(21) Appl. No.: 12/440,234

(22) PCT Filed: Sep. 6, 2007

(86) PCT No.: PCT/JP2007/067442
§ 371 (c)(1), (2), (4) Date: Mar. 5, 2009

(87) PCT Pub. No.: WO2008/029895
PCT Pub. Date: Mar. 13, 2008

(65) Prior Publication Data
US 2010/0179046 A1    Jul. 15, 2010

(30) Foreign Application Priority Data
Sep. 6, 2006  (JP) ................................ 2006-242191

(51) Int. Cl.
*G01N 27/26* (2006.01)
*C03C 3/095* (2006.01)
*C03C 3/15* (2006.01)

(52) U.S. Cl. .......... 204/416; 204/420; 204/433; 501/50; 501/64

(58) Field of Classification Search .................... 501/50, 501/51, 64, 78; 204/416, 417, 420, 433; 252/521.1
See application file for complete search history.

(56) References Cited

U.S. PATENT DOCUMENTS

| | | | | |
|---|---|---|---|---|
| 3,238,050 A | * | 3/1966 | Arthur et al. | 501/55 |
| 3,480,536 A | * | 11/1969 | Arthur | 204/420 |
| 4,052,285 A | * | 10/1977 | Dobson | 204/418 |
| 6,482,758 B1 | * | 11/2002 | Weber et al. | 501/41 |
| 2003/0127326 A1 | * | 7/2003 | Polikarpus et al. | 204/426 |

FOREIGN PATENT DOCUMENTS

| | | |
|---|---|---|
| CN | 1231998 A | 10/1999 |
| JP | 40-010560 | 5/1965 |
| JP | 40-012960 | 6/1965 |
| JP | 48-001097 | 1/1973 |
| JP | 59-069441 | 4/1984 |
| JP | 02-293343 | 4/1990 |

OTHER PUBLICATIONS

ISA Japan, International Search Report of PCT/JP2007/067442, Oct. 25, 2007, WIPO, 2pages Japan.

* cited by examiner

*Primary Examiner* — Noah Wiese
(74) *Attorney, Agent, or Firm* — Alleman Hall McCoy Russell & Tuttle LLP

(57) ABSTRACT

Disclosed is a sensitive glass for use in a pH-sensitive glass electrode, which comprises at least $Me_2O_3$ (Me represents a lanthanoid) and further comprises $Y_2O_3$ or $Sc_2O_3$ in an amount smaller than that of the $Me_2O_3$. Also disclosed is a sensitive glass for use in a cation-sensitive glass electrode, which comprises at least $Y_2O_3$ or $Sc_2O_3$.

19 Claims, 15 Drawing Sheets

GLASS ELECTRODE AND SENSITIVE GLASS FOR THE GLASS ELECTRODE

FIELD OF THE ART

This invention relates to an electrode for measuring an ion concentration such as a pH electrode and a pNa electrode, especially to a composition of its sensitive glass.

BACKGROUND ART

The sensitive glass of $SiO_2$ system, $Li_2O$ system used for, for example, the pH electrode requires various properties such as small in an alkali error, small in an acid error, a good response, and good chemical durability (in addition, other required properties can be represented by that potential gradient is close to a theoretical value, electric resistance is small, mechanical strength is high, and processing is easy).

Then conventionally various modified metals are blended in order to improve these properties. As an example to improve chemical durability (water resistance), it has been known to include a small amount of La as a trivalent metal in a composition of glass (non patent document 1).

La is filled into a net structure of the glass so as to tighten up on the net and contribute to improvement of water resistance by producing a hydrated gel layer having a constant layer. In addition, La is trivalent and its ionic diameter is relatively large, resulting in small electrostatic force of a univalent anion formed by oxygen square coordination. As a result, it is hardly sensitive to an alkali metal, namely hardly generates an alkali error. An example using another lanthanoid group instead of La has also been known for the same reason.

Non patent document 1: Shinnban pH no riron to sokuteihou (Theory and Measurement Methods for pH (New Edition)) (Maruzen Co. Ltd by H. Yoshimura etc.)

Patent document 1: Japan Patent Laid-open number 2-293343

DISCLOSURE OF THE INVENTION

Problems to be Solved by the Invention

However, the improvement in water resistance due to addition of La is just by comparison with the glass comprising no La, and practically it is required that the chemical durability (especially acid resistance or water resistance) and a responsiveness be superior. Since La is large in ionic diameter, electron affinity is relatively weak and strength to bond with oxygen is weak. This leads to an advantage that the alkali error is not caused, however, the force to tighten up on the hydrated gel layer is relatively weak and not only the chemical durability (especially, acid resistance and water resistance) is inferior to a certain degree but also the hydrated gel layer becomes thick, thereby generating a limit in improvement of the responsiveness.

The present claimed invention intends to satisfy the above requirement, and a main object of this invention is to improve the decay resistance and the responsiveness of the sensitive glass without degrading other properties.

Then, first the inventor of this invention performed experiments on the electrode using the trivalent rare metal (Y, Sc) whose atomic number is smaller than La instead of using La. The inventor thought the tightening effect on the hydrated gel layer became big because the ion diameter of the trivalent rare metal is small. However, the results showed otherwise; the alkali error was generated and a required measurement result was unable to obtain at pH 12 and over. The reason for this was considered to be that the ion diameter of the rare metal (Y, Sc) is smaller than that of La, the coulomb force (electrostatic force) of the rare metal (Y, Sc) is large, the electrostatic force of the univalent anion formed by oxygen square coordination also becomes large and it becomes sensitive to the alkali metal (Na or K) whose ion diameter is small in high alkali so that the alkali error becomes remarkable.

With this reason or not, there is no example practically using Y or Sc as the modified metal (speaking of a level of papers, in the patent document 1, there is a description that a rare earth metal (La, Y, Nd, Ce or the like) can be utilized, however, no experimental data is disclosed so that the description seems just to broaden the claim.). In addition, the rare earth metal is expensive. This may be one of the reasons why the rare earth metal such as Y or Sc has not been used.

Means to Solve the Problems

After repeating keen examinations, the inventor has completed this invention based on a conception that Me (Me represents lanthanoid (comprising La)) is added to Y or Sc.

More specifically, the pH-sensitive glass electrode in accordance with this invention is characterized by comprising at least $Me_2O_3$, and further comprising $Y_2O_3$ or $Sc_2O_3$ in an amount smaller than that of the $Me_2O_3$ as a composition of a sensitive glass used for the pH-sensitive glass electrode.

In accordance with this invention, it is possible to improve the acid resistance and water resistance or the responsiveness of the sensitive glass without degrading other properties (especially the alkali error).

As a reason why the responsiveness is improved, it can be conceived that, since Y or Sc is strong in the bonding force with oxygen because the electron affinity is strong and Y or Sc tightens the hydrated gel layer so as to make a thickness of the hydrated gel layer thin even though an amount of Y or Sc is small, it shortens the time required for the proton to diffuse in and pass through the hydrated gel layer so that improvement of the responsiveness is largely promoted. Then in case of automatic calibration after passing a certain time by immersing the glass electrode in the liquid to be measured like conventionally, since the output voltage is in a state more stable than that of the conventional glass electrode due to the improved responsiveness, it is possible to conduct an automatic calibration accurately with good repeatability, and eventually the repeatability or the sensitivity at a time of measurement is improved.

As a reason why the chemical durability is improved, it can be conceived that, since Y or Sc is smaller in the ion diameter and stronger in the electron affinity compared with La (or other lanthanoid), at a time when Y or Sc is filled into a net structure of the glass even though the amount is small, Y or Sc acts in an electrically repulsive manner against other cation ($Li^+$, $H_3O^+$ or the like) so that the other cation is prevented from passing the hydrated gel layer, thereby improving the chemical durability largely.

As a reason for enabling the alkali error to be small, it can be conceived that, since Y or Sc whose amount is smaller in a mol ratio than that of La is comprised in the sensitive glass in addition to La (or other lanthanoid), the effect from La dominates the alkali error so that a harmful effect on the alkali error by Y or Sc can be prevented.

Then the sensitivity and the repeatability of the sensitive glass can be improved by these operations and effects.

A concrete amount of $Y_2O_3$ or $Sc_2O_3$ to remarkably produce the above-mentioned operation and effect is obtained to a certain degree by the keen experiments by the inventor.

More specifically, speaking of a relationship between $Me_2O_3$ and $Y_2O_3$ or $Sc_2O_3$, it is preferable that a mole ratio of $Y_2O_3$ or $Sc_2O_3$ to $Me_2O_3$ is within 1/2~1/30. Speaking of an amount relative to whole of the sensitive glass, it is preferable that $Y_2O_3$ or $Sc_2O_3$ of 0.1 mol % and above is comprised. Speaking of the thickness of the hydrated gel layer formed on the surface of the sensitive glass, an amount of $Y_2O_3$ or $Sc_2O_3$ is preferable so as to make the thickness of the hydrated gel layer 60 nm or less in a stable state after the sensitive glass is immersed into water.

The above-mentioned sensitive glass is preferably a glass of lithium system.

It has been revealed that Sc has a specific property and it is difficult for Sc to produce the alkali error compared with Y. As a result, it can be conceivable that there is a case wherein $Me_2O_3$ such as $La_2O_3$ is not necessarily comprised as the composition for the sensitive glass.

Meanwhile, as mentioned above, in consideration of points wherein the univalent anion formed by the oxygen square coordination of Y or Sc has a large electrostatic force and is easily sensitive to the alkali metal (Na or K) ion whose ion diameter is small in high alkali, the sensitive glass can be applied to a responsive glass used for a cation-sensitive glass electrode (it goes without saying that proton is excluded from the cation.) if an amount of the Y or Sc to be comprised is increased. In this case, since the alkali error counts for nothing, Y or Sc may be comprised in the sensitive glass instead of La (or other lanthanoid). As a result, it is possible to obtain the sensitive glass whose decay resistance (especially, heat resistance, acid resistance) is high.

As the cation-sensitive glass electrode that can be considered to securely obtain this effect, a pNa sensitive glass electrode or a $pNH_4$ sensitive glass electrode may be represented.

Effect of the Invention

In accordance with this invention, it is possible for the sensitive glass to improve the decay resistance or the responsiveness and also to improve the sensitivity and the repeatability without degrading other properties.

EXPLANATION OF REFERENCE DESIGNATORS

1 . . . glass electrode
5 . . . sensitive glass

BEST MODES OF EMBODYING THE INVENTION

One embodiment of the present claimed invention will be explained.

Figure 1:
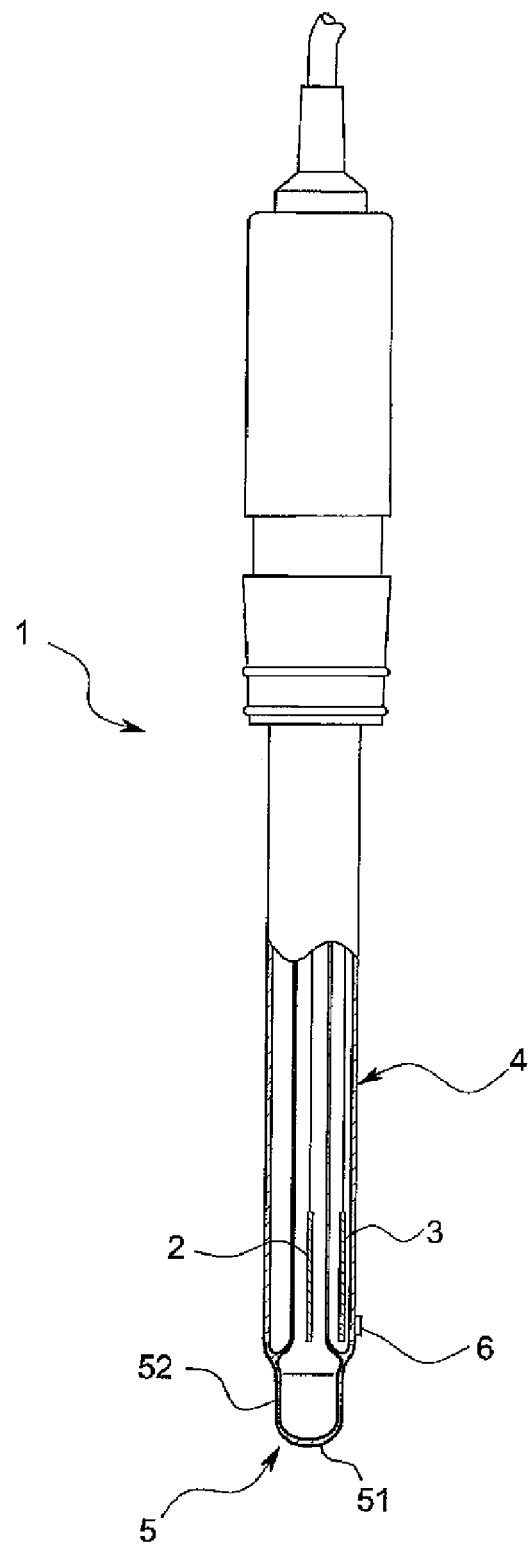
FIG. 1 is an overall configuration diagram of a pH-sensitive glass electrode in accordance with one embodiment of the present claimed invention.

A pH-sensitive glass electrode 1 in accordance with this embodiment is, as shown in FIG. 1, of a compound type, wherein an internal electrode 2 is integrally formed with a comparative electrode 3. In FIG. 1, the code 4 represents a support glass tube, the code 5 represents a sensitive glass and the code 6 represents a junction. In addition, a potassium chloride solution of a certain concentration is filled in the glass tube, and the internal electrode 2 and the comparative electrode 3 are immersed in the potassium chloride solution.

The sensitive glass 5 comprises $SiO_2$ as a main component (60~70 mol %), Li as an accessory component (25~32 mol %) and various modified metals (about 10 mol % in total) from a bottom surface 51 to a side surface 52. In this embodiment, at least $Me_2O_3$ is comprised and in addition to this, $Y_2O_3$ or $Sc_2O_3$ in an amount smaller than that of the $Me_2O_3$ is comprised as the modified metal.

It is acceptable that Me is lanthanoid (Eu, Ce, Nd, Gd or the like), and Me comprising $La_2O_3$ is more preferable from viewpoints of a past result that Me comprising $La_2O_3$ has been supplied to various products and a cost. In addition, a comprised amount of Me in whole of the sensitive glass is preferably about 2~6 mol %, and its upper limit is assumed to be about 10 mol % if elevation of electric resistance is taken into consideration.

If a comprised amount of $Y_2O_3$ or $Sc_2O_3$ relative to $Me_2O_3$ is too much, an alkali error exceeds a practical range. Contrary, if the comprised amount is too small, a responsive property cannot be exhibited. As a result, a range of its comprised amount of is given by itself. A thickness of a surface hydrated gel layer formed at a time of being immersed in water can be represented as a parameter to determine the responsive property. As mentioned above, it is considered that the responsive property is improved because the thinner the hydrated gel layer is, the more the time required for the proton to pass the gel layer is shortened. It is very much preferable to determine the lower limit of the comprised amount of $Y_2O_3$ or $Sc_2O_3$ so that a thickness of its hydrated gel layer becomes about 60 nm or less. A comprised amount (a molar ratio) of $Y_2O_3$ or $Sc_2O_3$ to the $Me_2O_3$ is preferably about 1/30~1/2, and more preferably about 1/3~1/6.

To comprise $Y_2O_3$ or $Sc_2O_3$ may mean to comprise $Y_2O_3$ alone, to comprise $Sc_2O_3$ alone, or to comprise a mixture of $Y_2O_3$ and $Sc_2O_3$ (in this case, a total molar quantity of $Y_2O_3$ and $Sc_2O_3$ is preferably about 1/30~1/2 of $Me_2O_3$).

Considering that Sc or Y forms a monadic anion whose electrostatic force is larger than that of La, this can be applied to not only the pH-sensitive glass electrode but also a sensitive glass for a cation-sensitive glass electrode (proton is excepted for cation). In this case, since the alkali error is of no importance, it should be considered to improve the responsiveness alone. As a result, Y or Sc may be comprised in the sensitive glass by completely substituting La.

It is acceptable that the comprised amount of $Y_2O_3$ or $Sc_2O_3$ is about 0.1 mol % or more, and its upper limit is not especially limited in view of a performance. However, the upper limit is preferably about 10 mol % or less from a viewpoint of a cost.

As a concrete sensitive glass represented are NAS11-18 system glass ($SiO_2$ system, $Na_2O$ 11 mol %, $Al_2O_3$ 18 mol %) used for a pNa electrode, and NAS27-4 system glass ($SiO_2$ system, $Na_2O$ 27 mol %, $Al_2O_3$ 4 mol %) used for $NH_4^+$ ionic electrode.

EMBODIMENT

One embodiment of the present claimed invention will be explained. It is a matter of course that the present claimed invention is not limited to this embodiment.

In this embodiment, six different kinds of sensitive glasses: a sensitive glass comprising $Y_2O_3$ (hereinafter referred to G2), and sensitive glasses comprising $Sc_2O_3$ (hereinafter referred to G3-1, G3-2, G3-3, G3-4, G3-5) were experimentally manufactured.

A composition of each G2, G3-1, G3-2, G3-3, G3-4 and G3-5 is as shown in the following Table 1.

TABLE 1

| sensitive glass | composition (mol %) | | | | | | | | |
|---|---|---|---|---|---|---|---|---|---|
| | $SiO_2$ | $Li_2O$ | $Y_2O_3$ | $Sc_2O_3$ | $La_2O_3$ | $Cs_2O$ | BaO | $Ta_2O_5$ | Total |
| G2 | 64 | 26 | 1 | — | 3 | 2 | 2 | 2 | 100 |
| G3-1 | 63.5 | 26 | — | 1.5 | 3 | 2 | 2 | 2 | 100 |
| G3-2 | 64 | 26 | — | 1 | 3 | 2 | 2 | 2 | 100 |
| G3-3 | 64.5 | 26 | — | 0.5 | 3 | 2 | 2 | 2 | 100 |
| G3-4 | 64.8 | 26 | — | 0.2 | 3 | 2 | 2 | 2 | 100 |
| G3-5 | 64.9 | 26 | — | 0.1 | 3 | 2 | 2 | 2 | 100 |

The sensitive glasses G2, G3-1, G3-2, G3-3, G3-4 and G3-5 were compared with conventional two kinds of sensitive glasses (hereinafter referred to G1-1, G1-2) regarding a responsiveness, an acid resistance and an alkali error.

A composition of each G1-1 and G1-2 is as shown in the following Table 2.

TABLE 2

| sensitive glass | composition (mol %) | | | | | | | |
|---|---|---|---|---|---|---|---|---|
| | $SiO_2$ | $Li_2O$ | $La_2O_3$ | $Cs_2O$ | BaO | $Ta_2O_5$ | $TiO_2$ | Total |
| G1-1 | 64 | 26 | 4 | 2 | 2 | 2 | — | 100 |
| G1-2 | 55 | 27.5 | 6 | — | 5.5 | — | 6 | 100 |

Figure 2:
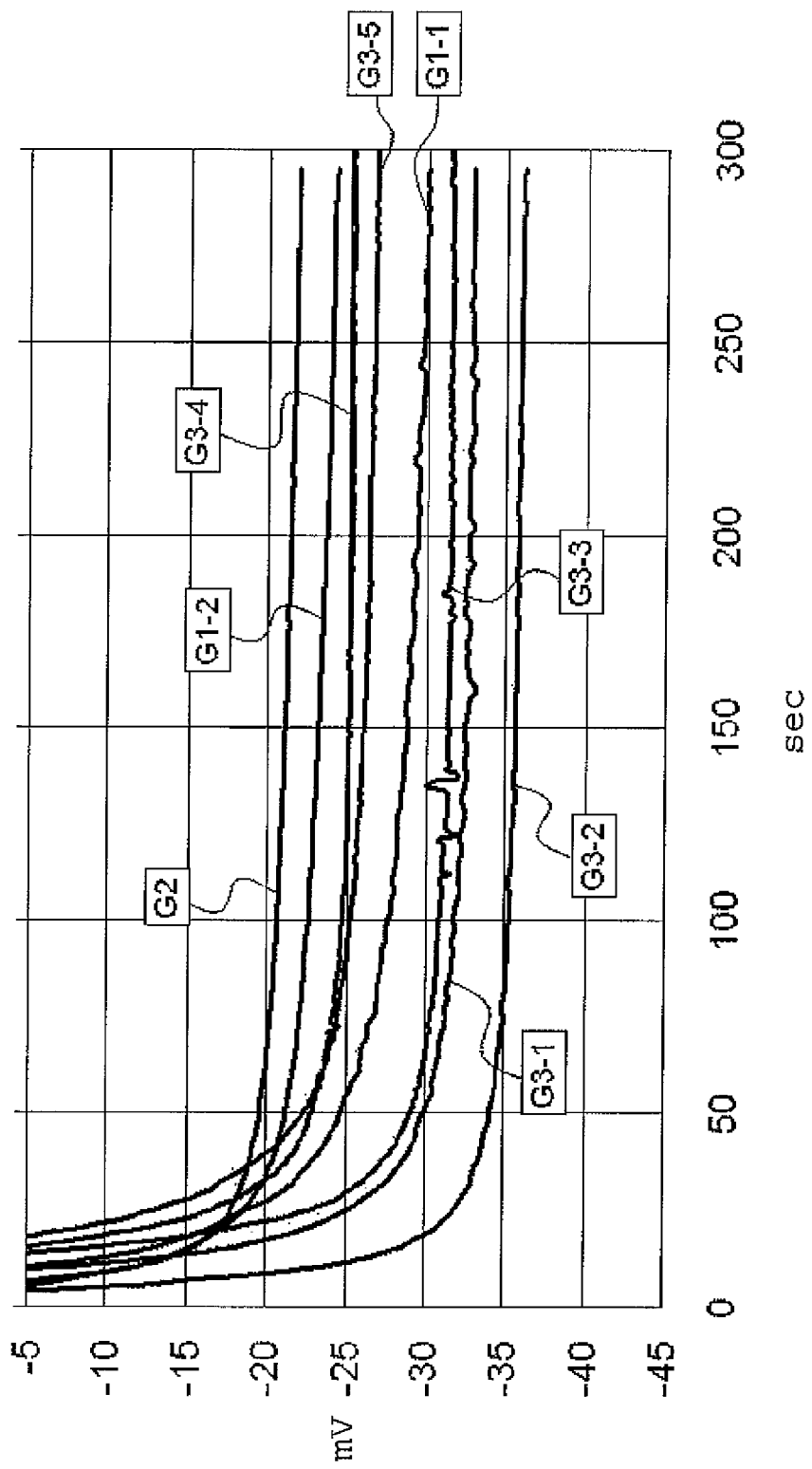
FIG. 2 is a graph showing a time change of an output voltage for each sensitive glass when Buffer pH4 (reference solution of pH4) is substituted by tap water in the embodiment of the present claimed invention.

Comparison data regarding a response rate for these sensitive glasses is shown in FIG. 2. A time change of an output voltage for each sensitive glass is compared when Buffer pH4 (reference solution of pH4) is substituted by tap water.

While each output voltage for G2, G3-1, G3-2, G3-3, G3-4 and G3-5 is generally statically determinate in 60 through 100 sec, it takes 200 sec or more for the conventional G1-1 and G1-2 to be statically determinate. Especially, quickness of the responsiveness for G3-1, G3-2, G3-3, G3-4 and G3-5 is noteworthy. The output voltage of G2, G3-1, G3-2, G3-3, G3-4 and G3-5 is in a far stable state compared with that of the conventional sensitive glass due to the improved responsiveness in case of conducting an automatic calibration at a time when a constant time (for example, 60 sec) has passed after immersing G2 and G3-1, G3-2, G3-3, G3-4 and G3-5 in a liquid to be measured. Then the automatic calibration can be conducted reproducibly and accurately, resulting in improving the reproducibility and sensitivity greatly at a time of measurement.

Figure 3:
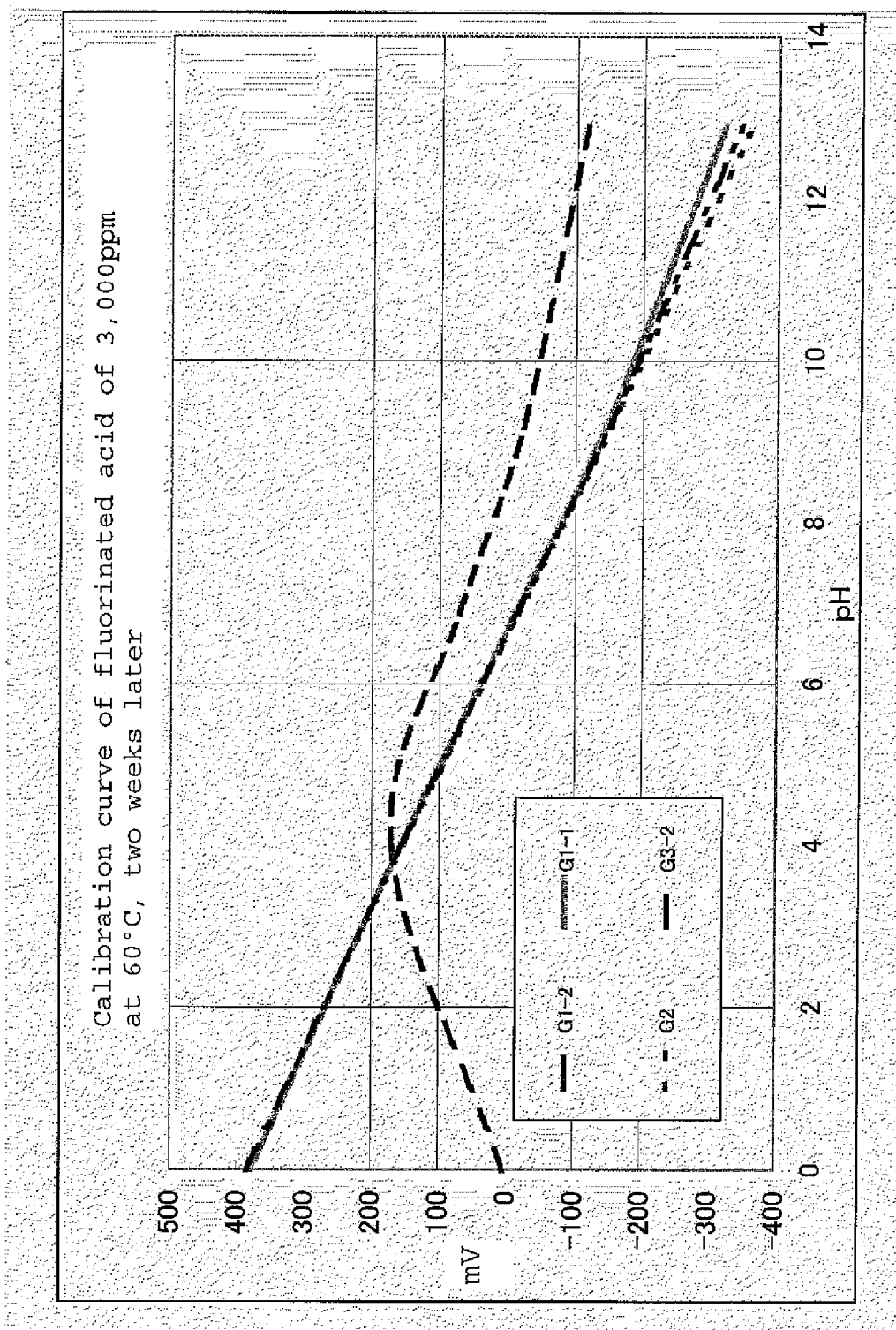
FIG. 3 is data showing an acid resistance and an alkali error for each sensitive glass after immersing the sensitive glasses in a solution of fluorinated acid of 3000 ppm at 60° C. for two weeks in this embodiment.

Next, comparison data regarding the acid resistance and the alkali error is shown in FIG. 3. Here shows the data after immersing G1-1, G1-2, G2 and G3-2 in a solution of fluorinated acid of 3000 ppm at 60° C. for two weeks. The acid resistance is greatly improved for G2, G3-2 compared with especially G1-2, and the alkali error is largely decreased for G2 and G3-2.

Figure 4:
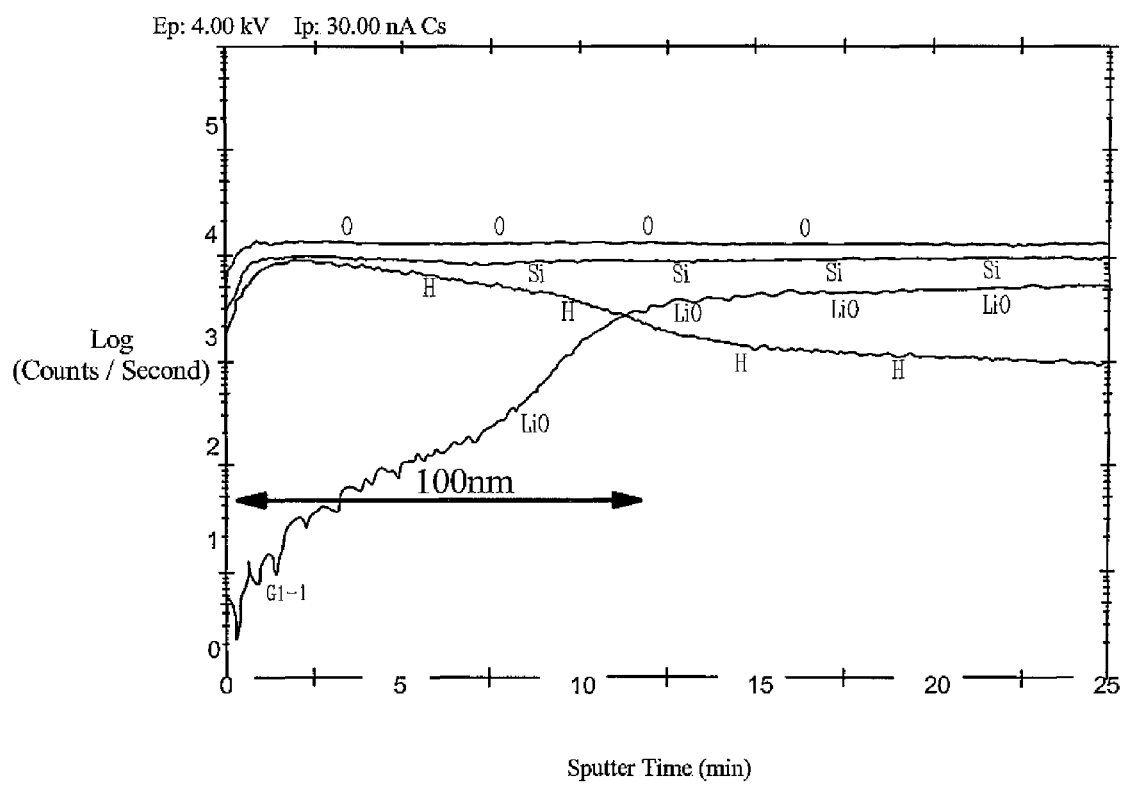
FIG. 4 is analytical data of a thickness of Lithium absentee layer of a conventional sensitive glass analyzed by the SIMS.
Figure 5:
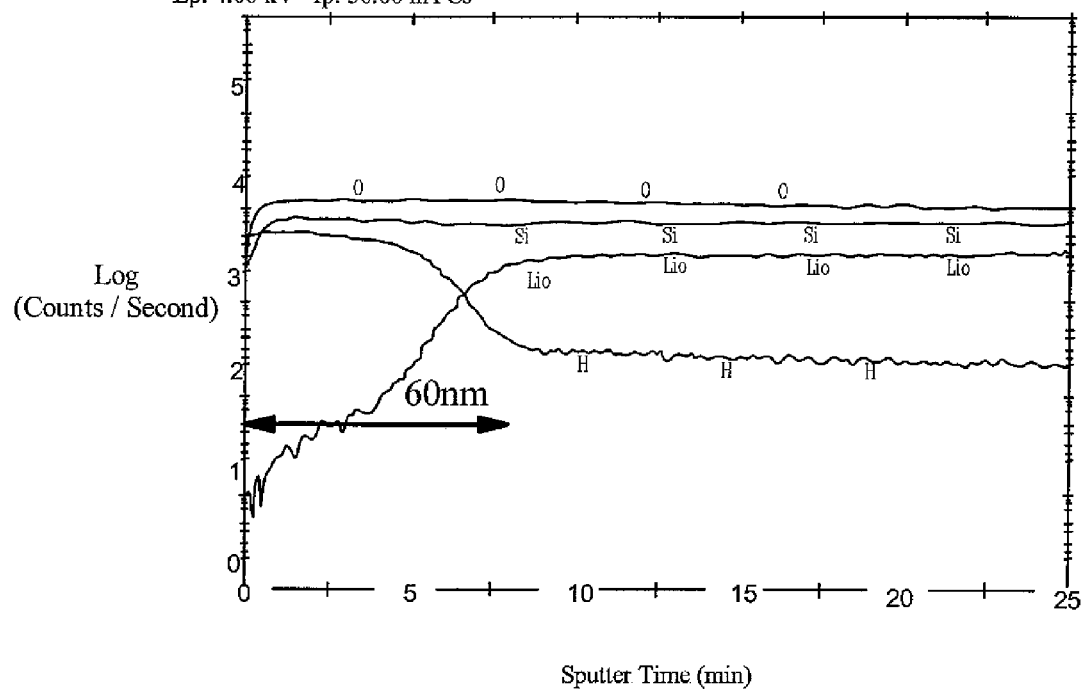
FIG. 5 is analytical data of a thickness of Lithium absentee layer of a G2 sensitive glass analyzed by the SIMS.
Figure 6:
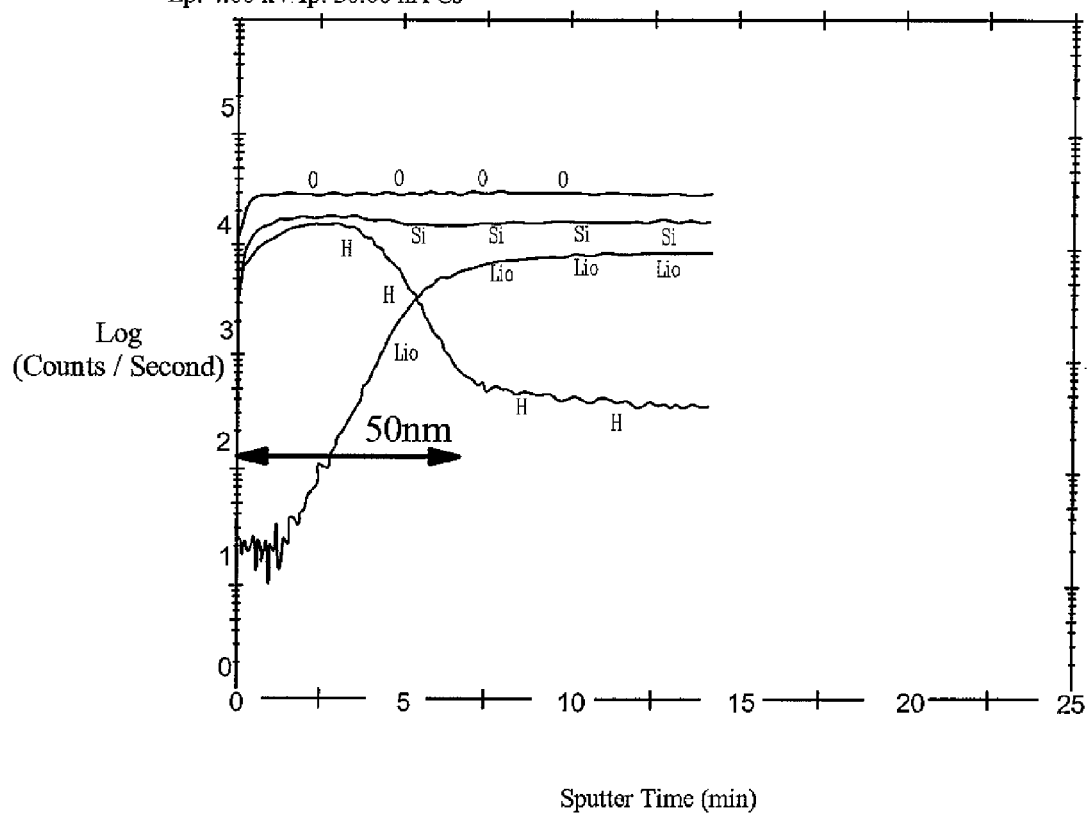
FIG. 6 is analytical data of a thickness of Lithium absentee layer of a G3 sensitive glass analyzed by the SIMS.

In addition, the verification data by the SIMS regarding a thickness of a hydrated gel layer is shown in FIG. 4 through FIG. 6.

As is clear from this data, it was revealed that an alkali (Li) absentee layer was formed in depth of about 100 nm from a surface for G1-1, about 60 nm for G2 and about 50 nm for G3-2. It is conceivable that the alkali absentee layer corresponds to the hydrated gel layer. Not only silanol group ($\equiv$Si—Ohio) but also $\equiv$Si—O—Li group remains in the alkali absentee layer, and it can be estimated that both of them contribute largely to an ion-exchange reaction. Ordinarily, it is said that the silanol group is formed on a surface of the glass in order to keep electric neutrality when the pH-sensitive glass film is immersed in water, and the silanol group is ion-exchanged in accordance with a proton concentration so that an interface potential generates. It is conceived that Li ion as being an ion carrier transfers in equilibrium by distributing the potential inside and outside of the surface of the glass film.

$$\equiv\text{Si}-\text{OH} \Leftrightarrow \equiv\text{Si}-\text{O}^- + \text{H}^+ \quad (1)$$

When pH of a specimen is alkalified, the expression (1) makes a shift to the right direction so that the specimen is negatively charged. Contrarily, when pH of the specimen is acidified, the expression (1) makes a shift to the left direction and a membrane potential fluctuates to positive in order to keep electric neutrality.

It can be estimated that $Li^+$ ion-bound with $\equiv$Si—$O^-$ is easily ionized when a residual group of $\equiv$Si—O—Li in the glass makes contact with acid so that a $\equiv$Si—$O^-$ site can be filled anytime.

G. Eisenman generally states that the response mechanism of the glass film is contributed by both the interface potential and the diffusion potential. It is conceivable in case that the proton diffuses in the glass, Li ions diffuse to the opposite direction in order to obtain the electric equilibrium and a diffusion potential is generated due to a difference of mobility between the proton and the Li ions. As a result, the hydrated layer can be considered to be a thickness of the diffused layer, and chances are high that an equilibrium velocity of the diffusion potential difference also contributes to the responsiveness. In either case, the thinner the hydrated layer is, the more likely the responsiveness is improved, and this accords the above-mentioned experimental result.

Furthermore, the experimental result of G3-3 will be explained.

In this experiment, solution substitution was conducted in the order of pure water washing→Buffer pH7→Buffer pH4→Buffer pH9→0.1 M NaOH→0.1M KOH→1M HCl→tap water. In order to examine the responsiveness of the pH electrode alone, a comparison electrode alone is immersed for 30 seconds in the sample to be used next so as to be stabilized prior to substituting the pH electrode. G3-3 in 0.1M NaOH showed less performance in the response speed alone compared with G3-2 and it turned out that the response speed was greatly improved for other case.

Figure 7:
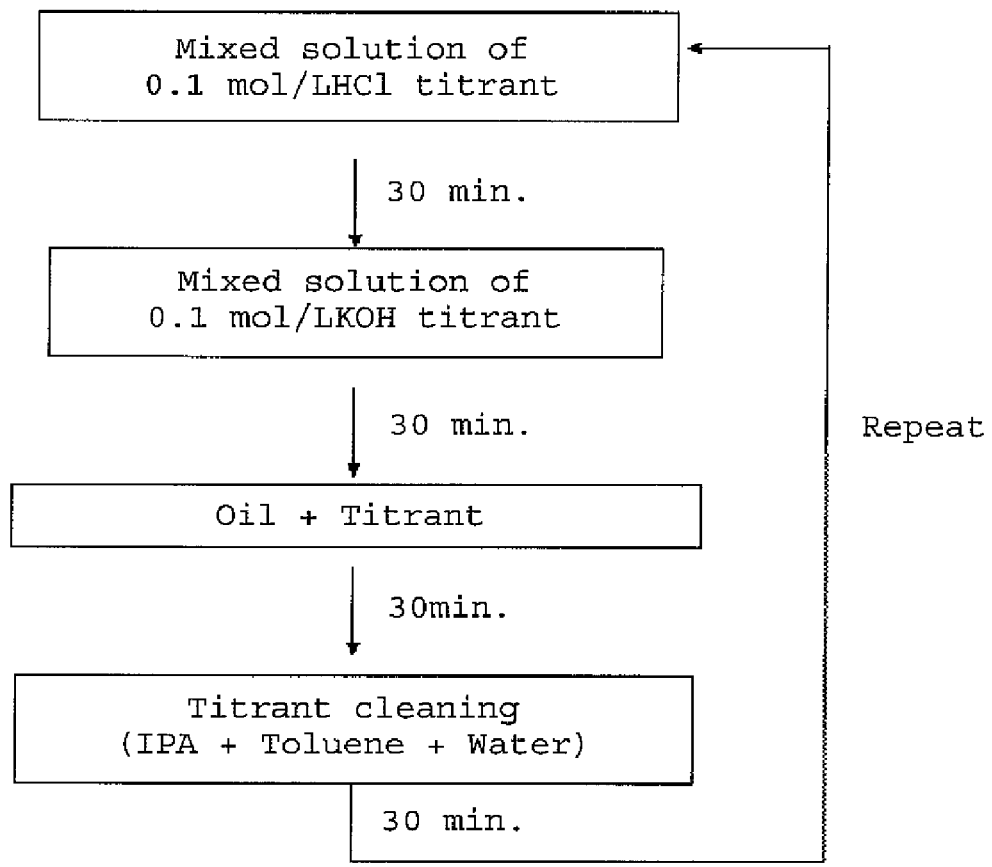
FIG. 7 is a measurement flow chart in conformity to an electrode check method specified by JIS K 2501.
Figure 8:
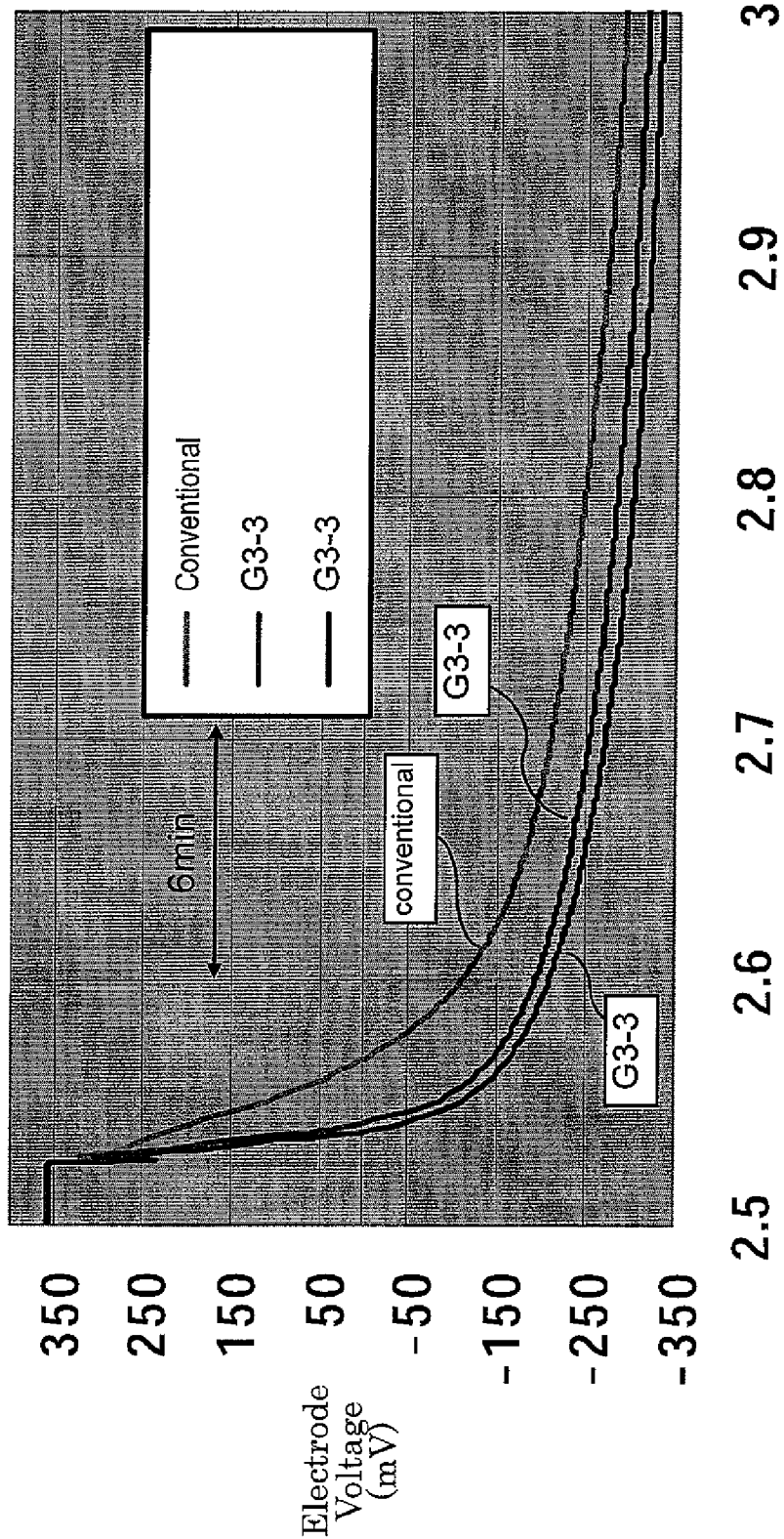
FIG. 8 is data to compare the responsiveness between a pH electrode using G3-3 sensitive glass and a conventional pH electrode (after one cycle).
Figure 9:
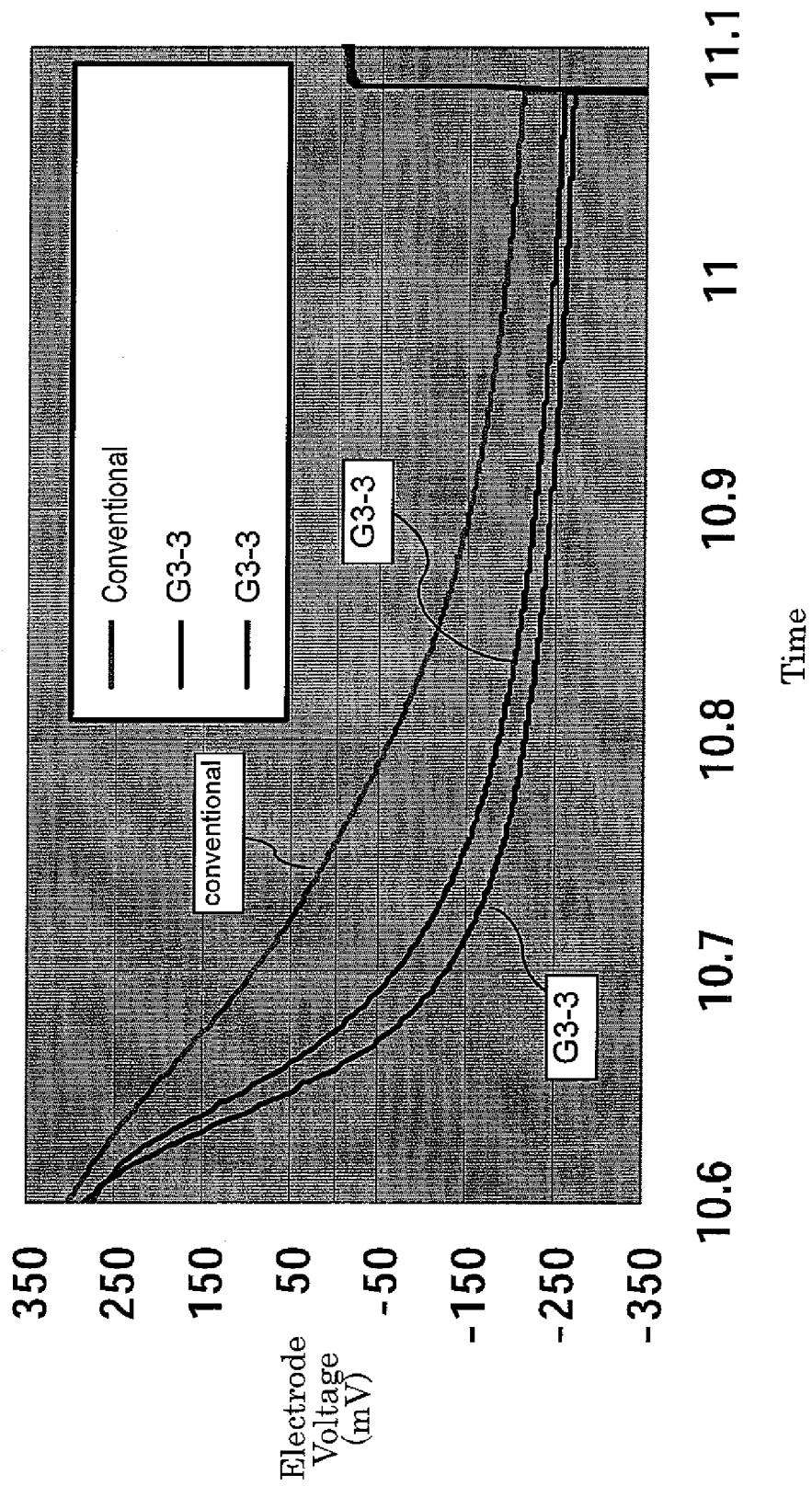
FIG. 9 is data to compare the responsiveness and decay resistance between the pH electrode using G3-3 sensitive glass and the conventional pH electrode (after five cycles).
Figure 10:
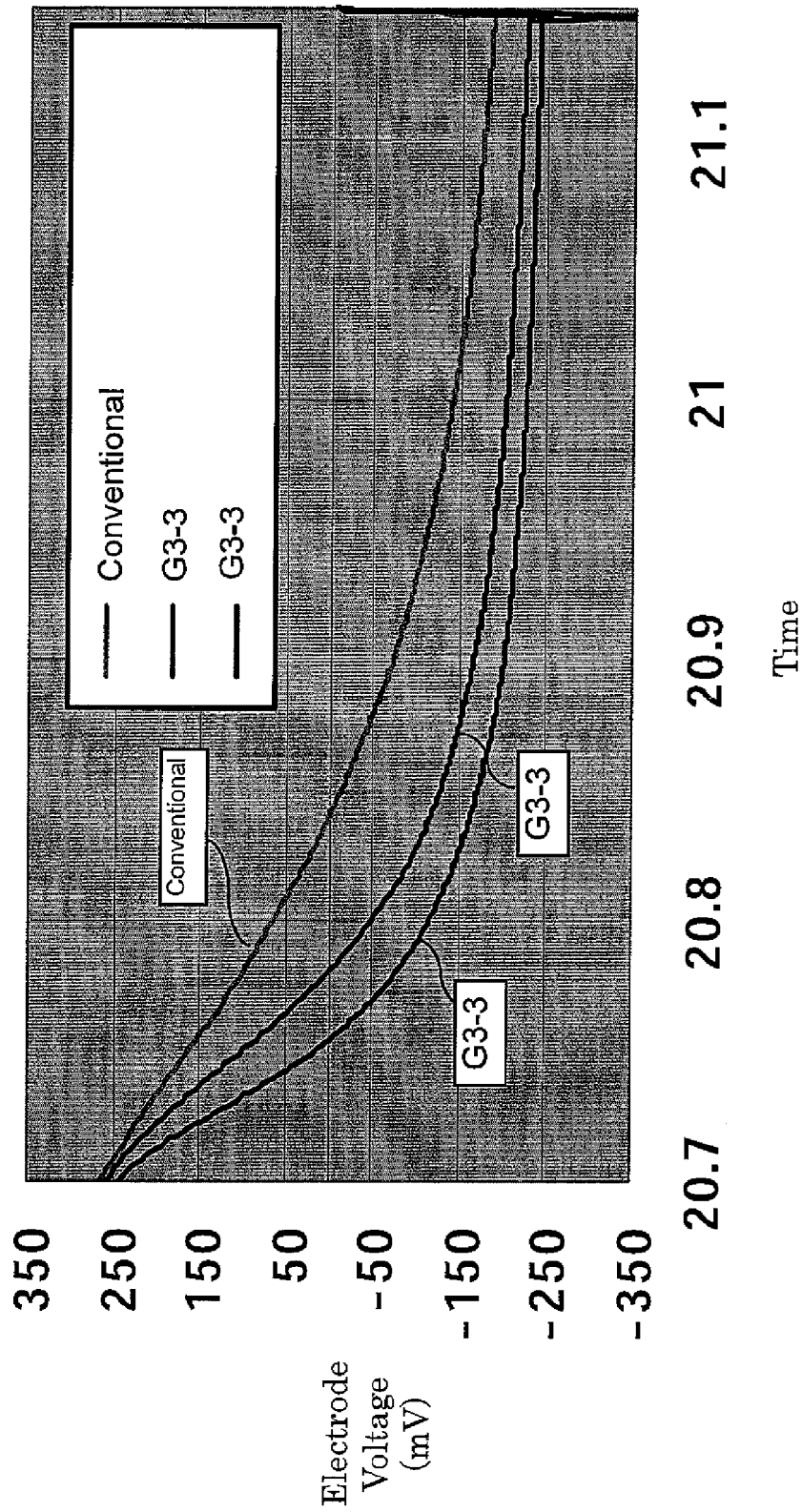
FIG. 10 is data to compare the responsiveness and decay resistance between the pH electrode using G3-3 sensitive glass and the conventional pH electrode (after ten cycles).
Figure 11:
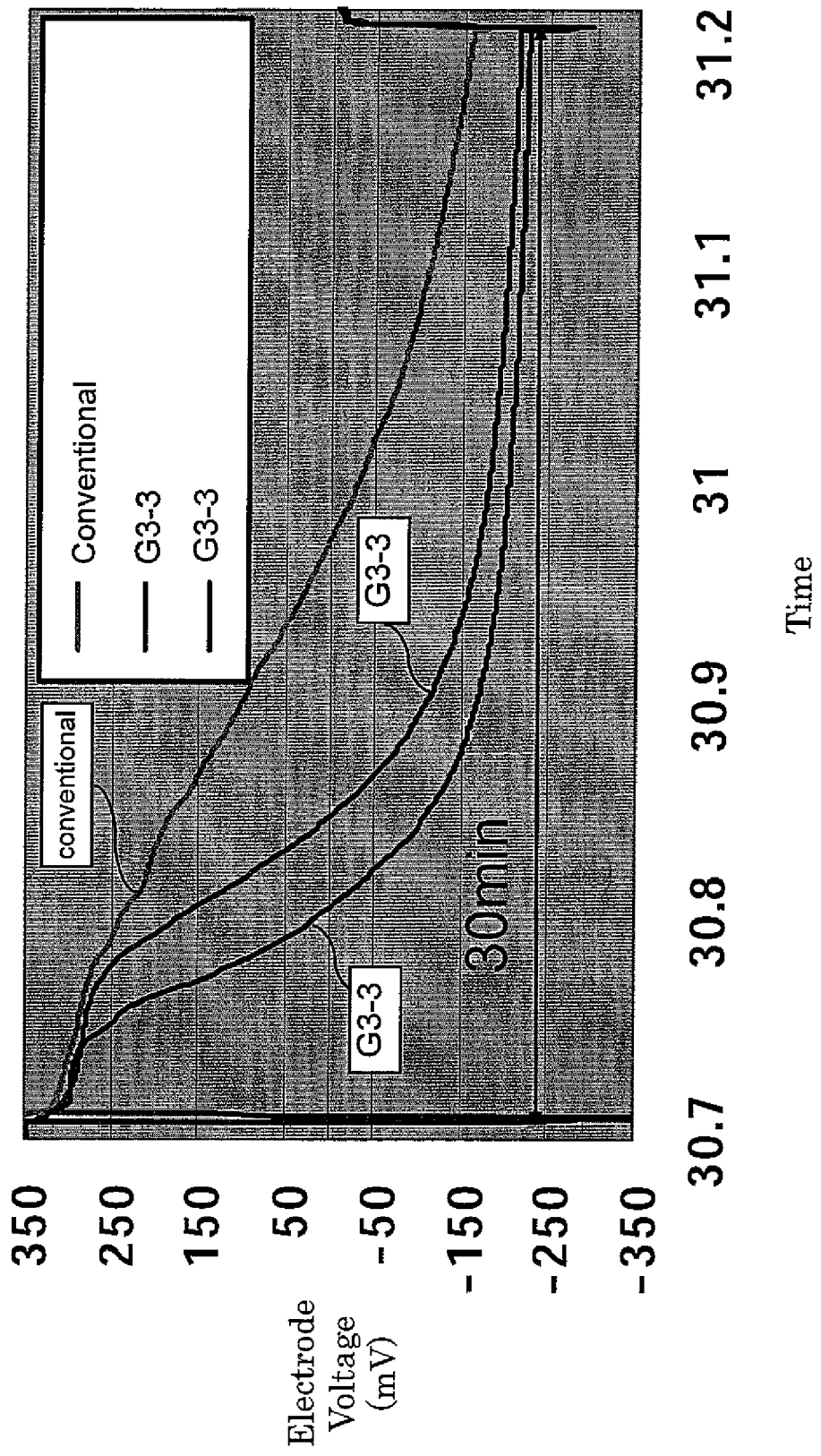
FIG. 11 is data to compare the responsiveness and decay resistance between the pH electrode using G3-3 sensitive glass and the conventional pH electrode (after fifteen cycles).

In addition, an experiment to compare the responsiveness and decay resistance was conducted on the pH electrode using G3-3 sensitive glass and the conventional pH electrode by means of the electrode check method according to the measurement flow chart shown in FIG. 7 with reference to JIS K 2501. The results are shown in FIG. 8 through FIG. 11.

When KOH of 0.1 mol/L is added to a titration solvent (IPA 49.5 mol %, toluene 50 mol %, water 0.5 mol %) as being a nonaqueous solvent, the pH electrode using G3-3 sensitive glass showed extremely high performance in responsiveness and decay resistance not only for aqueous solution but also for nonaqueous solvent compared with the conventional pH electrode as shown in FIG. 8 through FIG. 11.

Figure 12:
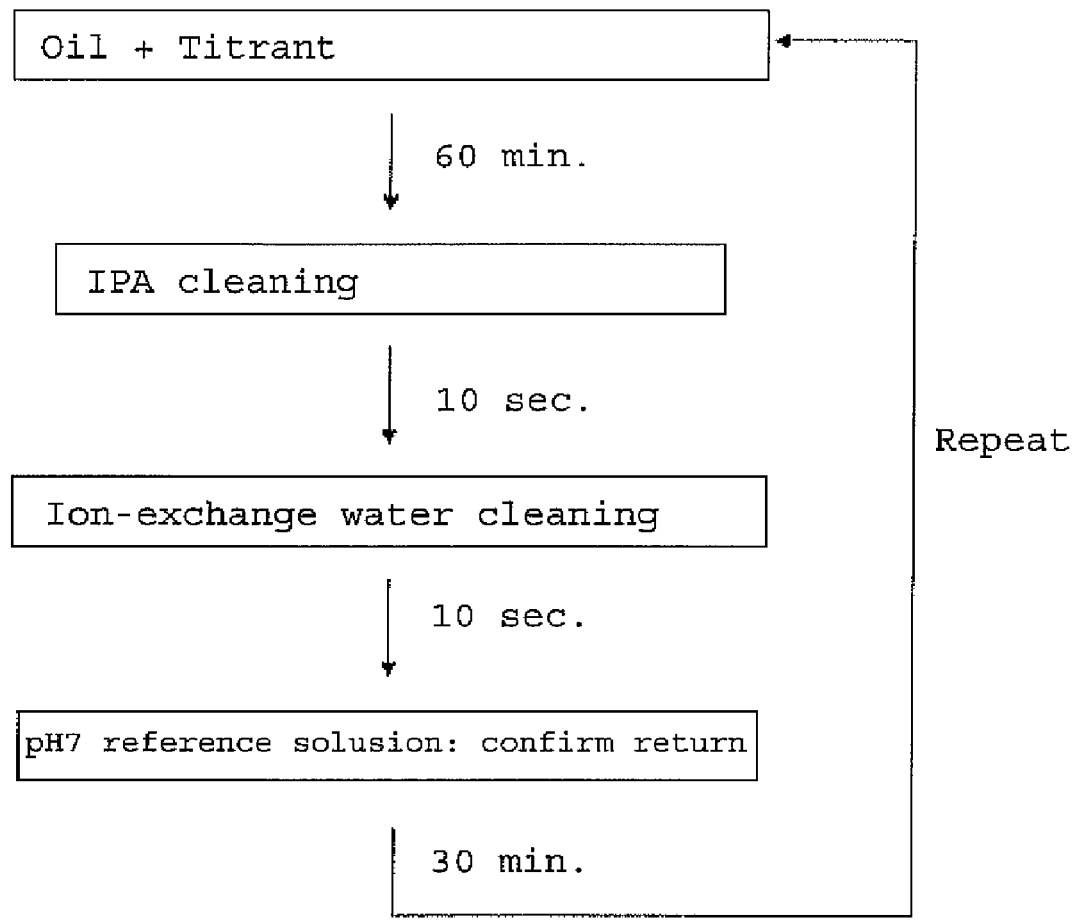
FIG. 12 is a measurement flow chart of a performance return test by substituting Buffer pH7 with oil.

In addition, an experiment to compare the return responsiveness in case that the electrode was immersed in a compound liquid of oil and the above-mentioned titration solvent, washed and then immersed in the Buffer pH7 (pH 7 reference solution) according to the measurement flow chart shown in FIG. 12 was conducted on the pH electrode using G3-3 sensitive glass and the conventional pH electrode. The result is shown in FIG. 13.

Figure 13:
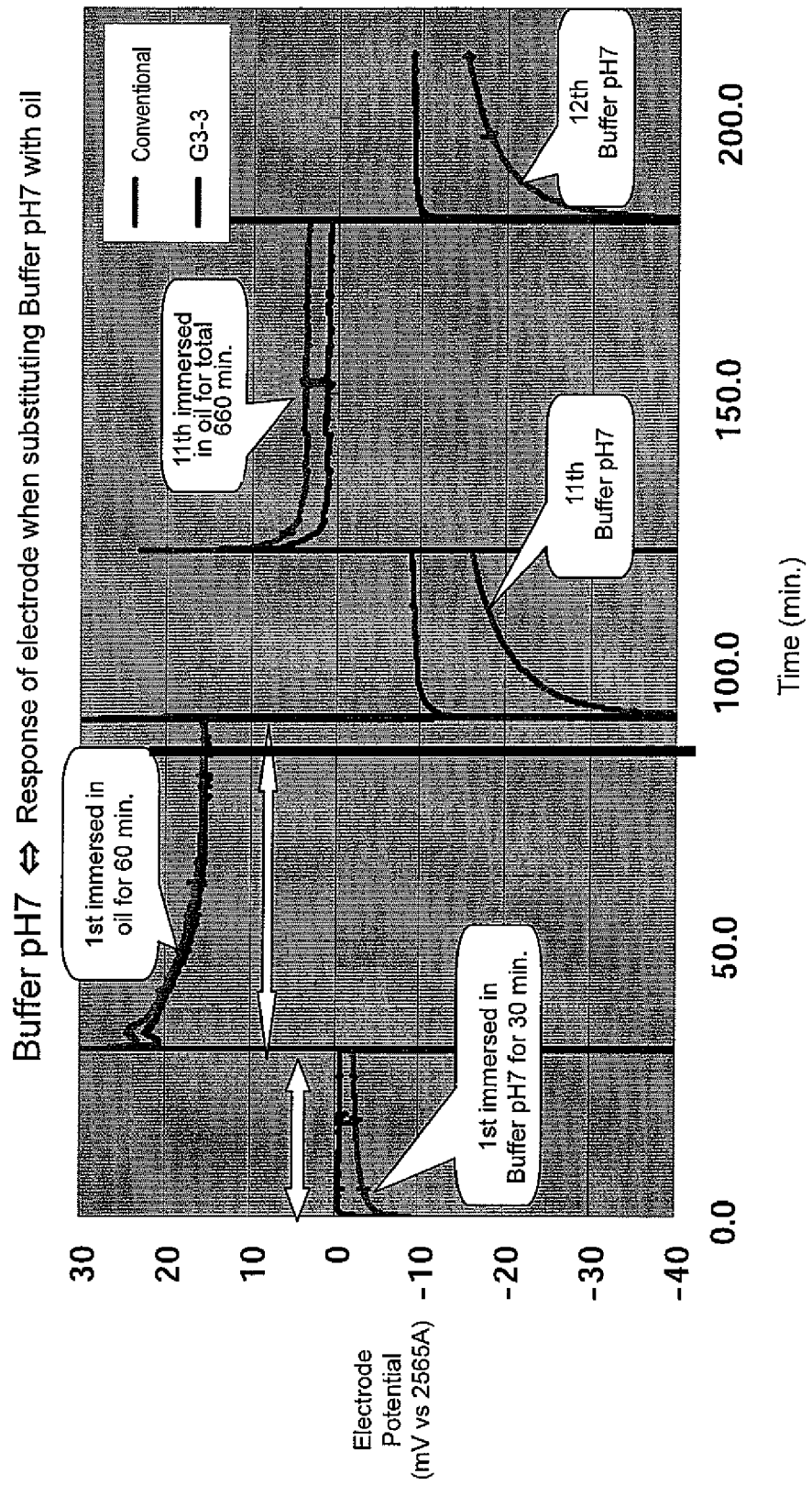
FIG. 13 is data to compare the return responsiveness and decay resistance between the pH electrode using G3-3 sensitive glass and the conventional pH electrode.

As shown in FIG. 13, the pH electrode using G3-3 sensitive glass showed overwhelmingly quick buffer return responsiveness after immersed in oil, and the response speed and decay resistance were largely improved for the pH electrode using G3-3 sensitive glass compared with those of the conventional pH electrode.

Next a relationship between a concentration of $Sc_2O_3$ and an alkali error (mV), a relationship between a concentration of $Sc_2O_3$ and a glass film resistance (MΩ), and a relationship between a concentration of $Sc_2O_3$ and a tap water sensitivity (s) were examined for each of the sensitive glasses G3-1, G3-2, G3-3, G3-4 and G3-5 comprising $Sc_2O_3$. The results are shown in the following table 3 through table 6. Multiple pH electrodes comprising each sensitive glass were prepared for verifying fluctuation.

TABLE 3

| sensitive glass | Sc2O3 Concentration (mol %) | alkali error (mV) | | | | | | | | | | |
|---|---|---|---|---|---|---|---|---|---|---|---|---|
| | | No. 1 | No. 2 | No. 3 | No. 4 | No. 5 | No. 6 | No. 7 | No. 8 | No. 9 | No. 10 | average |
| G3-1 | 1.5 | 9.6 | 10.1 | 9.4 | 9.6 | — | — | — | — | — | — | 9.7 |
| G3-2 | 1 | 9.4 | 9.6 | 9.6 | 9.9 | 9.9 | 9.4 | 9.8 | 9.6 | 9.4 | 9.4 | 9.6 |
| G3-3 | 0.5 | 9.5 | 9.8 | 9.4 | 9.6 | 10.1 | 10.4 | 10.4 | 10.7 | 10.9 | 10.4 | 10.1 |
| G3-4 | 0.2 | 8.1 | 7.9 | 8.3 | 7.9 | 8.0 | 8.4 | 8.3 | 8.5 | 8.3 | 8.4 | 8.2 |
| G3-5 | 0.1 | 7.5 | 7.1 | 7.2 | 7.3 | 7.3 | 7.4 | 7.7 | 7.8 | 7.4 | 7.4 | 7.4 |

TABLE 4

| sensitive glass | Sc2O3 Concentration (mol %) | glass film resistance (MΩ) | | | | | | | | | | |
|---|---|---|---|---|---|---|---|---|---|---|---|---|
| | | No. 1 | No. 2 | No. 3 | No. 4 | No. 5 | No. 6 | No. 7 | No. 8 | No. 9 | No. 10 | average |
| G3-1 | 1.5 | 88 | 99 | 75 | 79 | — | — | — | — | — | — | 85.3 |
| G3-2 | 1 | 80 | 90 | 84 | 83 | 74 | — | — | — | — | — | 82.2 |
| G3-3 | 0.5 | 126 | 114 | 125 | 140 | 113 | 141 | 128 | 105 | 132 | 80 | 120.4 |
| G3-4 | 0.2 | 130 | 105 | 90 | 120 | — | 110 | 140 | 100 | 115 | 110 | 113.3 |
| G3-5 | 0.1 | 155 | 81 | 140 | 100 | 115 | — | 135 | 175 | 95 | 79 | 119.4 |

TABLE 5

| sensitive glass | Sc2O3 Concentration (mol %) | tap water 90% sensitive(s) | | | | | | | | | | |
|---|---|---|---|---|---|---|---|---|---|---|---|---|
| | | No. 1 | No. 2 | No. 3 | No. 4 | No. 5 | No. 6 | No. 7 | No. 8 | No. 9 | No. 10 | average |
| G3-1 | 1.5 | 18 | 18 | 16 | 18 | — | — | — | — | — | — | 17.5 |
| G3-2 | 1 | 8 | 13 | 10 | 13 | 5 | 13 | 15 | 13 | 10 | 10 | 11.0 |
| G3-3 | 0.5 | 13 | 8 | 11 | 12 | 13 | 12 | 12 | 12 | 19 | 13 | 12.5 |
| G3-4 | 0.2 | 18 | 18 | 16 | 18 | 17 | 14 | 15 | 14 | 13 | 11 | 15.4 |
| G3-5 | 0.1 | 18 | 14 | 11 | 18 | 15 | 13 | 13 | 14 | 14 | 12 | 14.2 |

TABLE 6

| sensitive glass | Sc2O3 Concentration (mol %) | tap water 98% sensitive(s) | | | | | | | | | | |
|---|---|---|---|---|---|---|---|---|---|---|---|---|
| | | No. 1 | No. 2 | No. 3 | No. 4 | No. 5 | No. 6 | No. 7 | No. 8 | No. 9 | No. 10 | average |
| G3-1 | 1.5 | 62 | 48 | 43 | 64 | — | — | — | — | — | — | 54.3 |
| G3-2 | 1 | 28 | 45 | 30 | 35 | 18 | 55 | 63 | 58 | 45 | 43 | 42.0 |
| G3-3 | 0.5 | 35 | 28 | 33 | 31 | 37 | 38 | 41 | 37 | 44 | 36 | 36.0 |
| G3-4 | 0.2 | 48 | 41 | 38 | 43 | 35 | 50 | 47 | 44 | 50 | 30 | 42.6 |
| G3-5 | 0.1 | 55 | 46 | 42 | 53 | 50 | 51 | 55 | 54 | 50 | 51 | 50.7 |

As shown in the above Table 3, the Alkali error showed a tendency that the less the composition of $Sc_2O_3$ in the sensitive glass was, the less an effect of the Alkali error was.

As shown in the above Table 4, the glass film resistance showed a tendency that the more the composition of $Sc_2O_3$ in the sensitive glass was, the smaller the glass film resistance was.

As shown in the above Table 5 and Table 6, the tap water sensitivity showed that the sensitivity was especially superior for a case that the composition of $Sc_2O_3$ in the sensitive glass was about 0.5~1 mol %.

Furthermore, a deterioration test by means of the sterilization in place (SIP) (130° C. sterilization by steam) was conducted on a pH electrode comprising the sensitive glass G2' whose composition is shown in the following Table 7 ($La_2O_3$ of 4.5 mol % is blended in order to develop the alkali resistance), a pH electrode comprising the sensitive glass G2 and a pH electrode comprising G3-3 by repeatedly immersing each of the pH electrodes into a sterile autoclave (130° C.) and sensitive deterioration was monitored. The results are shown in FIG. 14 and FIG. 15.

TABLE 7

| sensitive glass | composition (mol %) | | | | | | | |
|---|---|---|---|---|---|---|---|---|
| | $SiO_2$ | $Li_2O$ | $Y_2O_3$ | $La_2O_3$ | $Cs_2O$ | BaO | $Ta_2O_5$ | Total |
| G2' | 60 | 26 | 1.5 | 4.5 | 2.5 | 2.5 | 3 | 100 |

Figure 14:
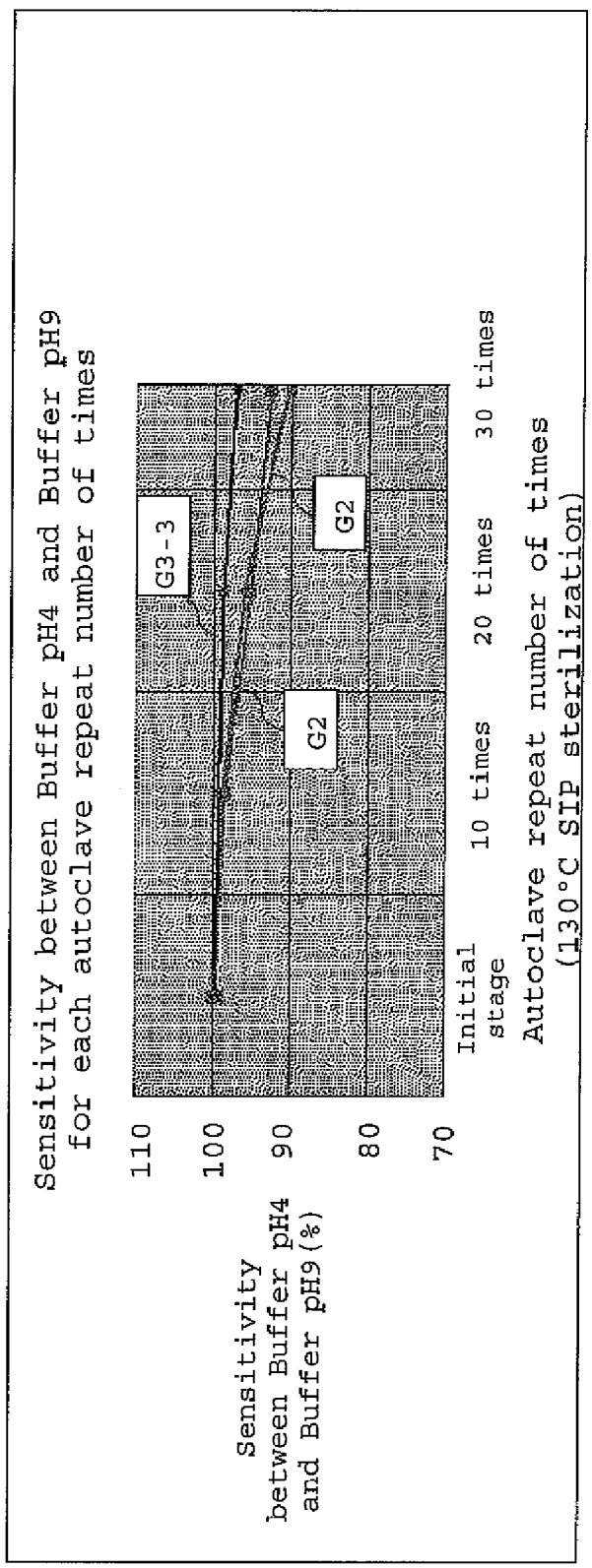
FIG. 14 is data to compare the deterioration test results (sensitivity between Buffer pH4 and Buffer pH9) of the pH electrodes using G2', G2 and G3-3 sensitive glass.
Figure 15:
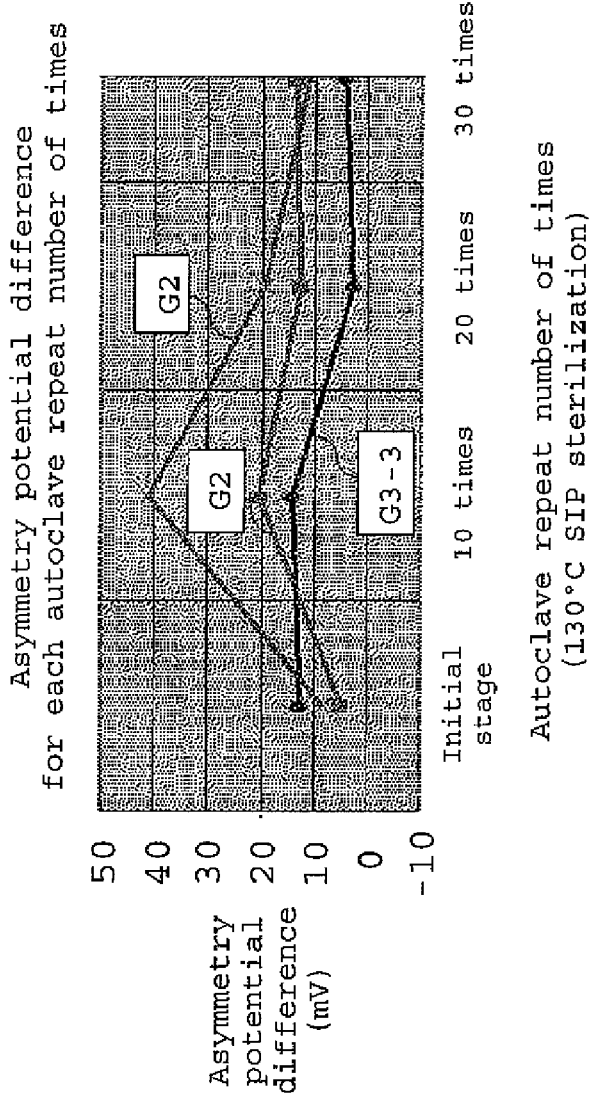
FIG. 15 is data to compare the deterioration test results (asymmetry potential) of the pH electrodes using G2', G2 and G3-3 sensitive glass.

As shown in FIG. 14 and FIG. 15, sensitive deterioration was restrained for all of the pH electrodes, and almost no asymmetry potential was generated. Especially for the pH electrode comprising G3-3, more than 90% sensitivity could be maintained and the asymmetry potential could be restrained after repeating the test 50 times In addition, the present claimed invention may be variously modified by appropriately combining each explained arrangement without departing from its spirit.

The invention claimed is:

1. A pH electrode, comprising an ion sensitive glass comprising at least $Li_2O$ and $Me_2O_3$ (wherein Me represents a lanthanoid) and further comprising $Y_2O_3$ or $Sc_2O_3$ in an amount smaller than that of the $Me_2O_3$.

2. The pH electrode described in claim 1, wherein a mole ratio of $Y_2O_3$ or $Sc_2O_3$ to $Me_2O_3$ is within 1/2~1/30 in the ion sensitive glass.

3. The pH electrode described in claim 1, wherein the ion sensitive glass comprises $Y_2O_3$ or $Sc_2O_3$ of 0.1 mol % and above.

4. A pNa electrode, comprising an ion sensitive glass comprising at least either $Na_2O$ or $Li_2O$ and $Sc_2O_3$.

5. A pNH4 electrode, comprising an ion sensitive glass comprising at least either $Na_2O$ or $Li_2O$ and $Sc_2O_3$.

6. A pH electrode, comprising an ion sensitive glass comprising at least $Li_2O$ and $Sc_2O_3$.

7. The pH electrode described in claim 1, further comprising:
an internal electrode; and
a support tube containing the internal electrode with a potassium chloride solution, wherein
the ion sensitive glass is connected to a distal end section of the support tube.

8. The pNa electrode described in claim 4, further comprising:
an internal electrode; and
a support tube containing the internal electrode with a potassium chloride solution, wherein
the ion sensitive glass is connected to a distal end section of the support tube.

9. The pNH4 electrode described in claim 5, further comprising:
an internal electrode; and
a support tube containing the internal electrode with a potassium chloride solution, wherein
the ion sensitive glass is connected to a distal end section of the support tube.

10. A pH electrode, comprising:
an ion sensitive glass comprising at least $Li_2O$ and $Me_2O_3$ (wherein Me represents a lanthanoid) and further comprising $Sc_2O_3$ in an amount smaller than that of the $Me_2O_3$.

11. The pH electrode described in claim 10, wherein a mole ratio of $Sc_2O_3$ to $Me_2O_3$ is within 1/2~1/30 in the ion sensitive glass.

12. The pH electrode described in claim 10, wherein the ion sensitive glass comprises $Y_2O_3$ of 0.1 mol % and above.

13. The pH electrode described in claim 10, further comprising:
an internal electrode; and
a support tube containing the internal electrode with a potassium chloride solution, wherein
the ion sensitive glass is connected to a distal end section of the support tube.

14. A pH electrode, comprising:
an ion sensitive glass comprising at least $Li_2O$ and $La_2O_3$ of 2~10 mol % and further comprising $Y_2O_3$ in an amount smaller than that of the $La_2O_3$.

15. The pH electrode described in claim 14, wherein a mole ratio of $Y_2O_3$ to $La_2O_3$ is within 1/2~1/30 in the ion sensitive glass.

16. The pH electrode described in claim 14, wherein the ion sensitive glass comprises $Y_2O_3$ of 0.1 mol % and above.

17. The pH electrode described in claim 14, further comprising:
an internal electrode; and
a support tube containing the internal electrode with a potassium chloride solution, wherein
the ion sensitive glass is connected to a distal end section of the support tube.

18. A pNa or pNH$_4$ electrode, comprising an ion sensitive glass comprising at least either Na$_2$O or Li$_2$O and La$_2$O$_3$ of 2~10 mol % and further comprising Y$_2$O$_3$ in an amount smaller than that of the La$_2$O$_3$.

19. The pNa or pNH$_4$ electrode as described in claim 18, further comprising:
an internal electrode; and
a support tube containing the internal electrode with a potassium chloride solution, wherein
the ion sensitive glass is connected to a distal end section of the support tube.

* * * * *

UNITED STATES PATENT AND TRADEMARK OFFICE
CERTIFICATE OF CORRECTION

| | | |
|---|---|---|
| PATENT NO. | : 8,262,877 B2 | Page 1 of 1 |
| APPLICATION NO. | : 12/440234 | |
| DATED | : September 11, 2012 | |
| INVENTOR(S) | : Iwamoto et al. | |

It is certified that error appears in the above-identified patent and that said Letters Patent is hereby corrected as shown below:

On the title page, Item [73] delete "HORIBA STEC, Co., Ltd." and insert --HORIBA, Ltd.--.

Signed and Sealed this
Twenty-fifth Day of March, 2014

Michelle K. Lee
*Deputy Director of the United States Patent and Trademark Office*